(12) United States Patent
Bedoukian

(10) Patent No.: US 9,314,029 B2
(45) Date of Patent: Apr. 19, 2016

(54) CONTROL AND REPELLENCY OF MOSQUITOES

(71) Applicant: BEDOUKIAN RESEARCH, INC., Danbury, CT (US)

(72) Inventor: Robert H. Bedoukian, West Redding, CT (US)

(73) Assignee: Bedoukain Research, Inc., Danbury, CT (US)

( * ) Notice: Subject to any disclaimer, the term of this patent is extended or adjusted under 35 U.S.C. 154(b) by 0 days.

(21) Appl. No.: 14/391,248

(22) PCT Filed: Apr. 30, 2013

(86) PCT No.: PCT/US2013/000121
§ 371 (c)(1),
(2) Date: Oct. 8, 2014

(87) PCT Pub. No.: WO2013/165477
PCT Pub. Date: Nov. 7, 2013

(65) Prior Publication Data
US 2015/0133540 A1     May 14, 2015

Related U.S. Application Data

(60) Provisional application No. 61/687,919, filed on May 2, 2012.

(51) Int. Cl.
*A01N 49/00*     (2006.01)
*A01N 31/06*     (2006.01)
(Continued)

(52) U.S. Cl.
CPC .............. *A01N 49/00* (2013.01); *A01N 31/06* (2013.01); *A01N 35/06* (2013.01); *A01N 37/02* (2013.01);
(Continued)

(58) Field of Classification Search
CPC ..................................................... A01N 49/00
USPC ........................................................ 514/460
See application file for complete search history.

(56) References Cited

U.S. PATENT DOCUMENTS

| 4,332,941 A | 6/1982 | Berthold et al. |
| 5,091,423 A | 2/1992 | Wilson et al. |

(Continued)

FOREIGN PATENT DOCUMENTS

| EP | 0 078 641 A1 | 5/1983 |
| EP | 0 167 266 A1 | 1/1986 |

(Continued)

OTHER PUBLICATIONS

IPRP dated Nov. 13, 2014 from corresponding PCT Application No. PCT/US2013/000121, 8 pages.
(Continued)

*Primary Examiner* — Taofiq A Solola
(74) *Attorney, Agent, or Firm* — Ohlandt, Greeley, Ruggiero & Perle, L.L.P.

(57) ABSTRACT

Control or repellency of mosquitoes is accomplished by bringing the insects into contact with at least one of the compounds of the structure (I)

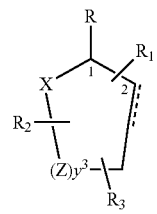

wherein
R is selected from —OH, =O, —OC(O)R$_4$, —OR$_6$, —(OR$_6$)$_2$, wherein each R$_6$ is independently selected from an alkyl group containing from 1 to 4 carbon atoms and R$_4$ is a branched or straight chain, saturated or unsaturated hydrocarbyl group with zero to two double bonds and from 1 to 15 carbon atoms;
X is O or CH$_2$, with the proviso that when X is O R can only be =O;
each Z is independently selected from (CH) and (CH$_2$);
y is a numeral selected from 1 and 2;
R$_1$ is selected from H or a branched or straight chain, saturated or unsaturated hydrocarbyl group with zero to two double bonds and from 1 to 15 carbon atoms;
R$_2$ is selected from H and a branched or straight chain, saturated or unsaturated hydrocarbyl group with zero to three double bonds and from 1 to 15 carbon atoms;
R$_3$ is selected from the group consisting of H and a branched or straight chain, saturated or unsaturated hydrocarbyl group with zero to three double bonds and from 1 to 15 carbon atoms, —(CH$_2$)$_n$OH, —C(O)OR$_5$, —CH$_2$C(O)OR$_7$, —CH$_2$C(O)R$_8$, —C(O)NR$_9$R$_{10}$, —CH$_2$C(O)NR$_{11}$R$_{12}$ where each of R$_5$, R$_7$, R$_8$, R$_9$, R$_{10}$, R$_{11}$ and R$_{12}$ is independently selected from H and a branched or straight chain, saturated or unsaturated hydrocarbyl group with zero to three double bonds and from 1 to 15 carbon atoms and n is an integer of from 1 to 12;
the bond between the 2 and 3 positions in the ring structure may be a single or a double bond; and
wherein the compounds of structure (I) contain from 11 to 20 total carbon atoms in the compounds, with the proviso that when R is =O, X is CH$_2$, Z is CH$_2$, y is 1 R$_2$ is H, and R$_3$ is CH$_2$C(O)OR$_7$ then the total number of carbon atoms in the compounds of structure (I) is from 15 to 20 carbon atoms, and when X is O and R is =O the total number of carbon atoms in the compounds of structure (I) is from 11 to 17 carbon atoms. The invention also includes optical isomers, diastereomers and enantiomers of the named structures. Thus, at all stereocenters where stereochemistry is not explicitly defined, all possible epimers are envisioned.

12 Claims, No Drawings

(51) Int. Cl.

| | | |
|---|---|---|
| *A01N 35/06* | (2006.01) | |
| *A01N 37/02* | (2006.01) | |
| *A01N 37/18* | (2006.01) | |
| *A01N 43/08* | (2006.01) | |
| *A01N 43/16* | (2006.01) | |
| *A01N 37/36* | (2006.01) | |
| *A01N 37/42* | (2006.01) | |

(52) U.S. Cl.
CPC ............... *A01N 37/18* (2013.01); *A01N 37/36* (2013.01); *A01N 37/42* (2013.01); *A01N 43/08* (2013.01); *A01N 43/16* (2013.01)

(56) References Cited

U.S. PATENT DOCUMENTS

| | | | |
|---|---|---|---|
| 5,118,711 | A | 6/1992 | Wilson et al. |
| 6,060,507 | A | 5/2000 | Hill et al. |
| 6,660,288 | B1 | 12/2003 | Behan et al. |
| 7,622,498 | B2 | 11/2009 | Justino et al. |
| 8,551,510 | B2 | 10/2013 | Bedoukian et al. |
| 2007/0196412 | A1 | 8/2007 | Karl et al. |
| 2010/0278755 | A1 | 11/2010 | Dell |
| 2011/0124877 | A1 | 5/2011 | Ito et al. |
| 2012/0046359 | A1 | 2/2012 | Bedoukian |

FOREIGN PATENT DOCUMENTS

| | | | |
|---|---|---|---|
| JP | S6348203 | A | 2/1988 |
| WO | 2009034352 | A1 | 3/2009 |

OTHER PUBLICATIONS

International Search Report dated Jul. 12, 2013 from PCT/US2013/000121, 3 pages.
Written Opinion dated Jul. 12, 2013 from PCT/US2013/000121, 13 pages.
Chinese Notification of the First Office Action dated Oct. 27, 2015 from corresponding Chinese Patent Application No. 201380022551. X, 21 pages.
European Office Action dated Nov. 30, 2015 from corresponding EP Application No. 13784978.2, 7 pages.
Couladouros, et al.; "A General Synthetic Route Towards γ and σ-Lactones. Total Asymmetric Synthesis of (−)—Vluricatacin and the Mosquito Oviposition Pheromone (5R,6S)-6-Acetoxy-hexadecanolide"; Tetrahedron Letters 40, 1999, pp. 4861-4862.
Smallegange et al.; "Identification of candidate volatiles that affect the behavioural response of the malaria mosquito Anopheles gambiae sensu stricto to an active kairornone blend: laboratory and semi-field assays"; Physiological Entomology, 2012, 37, pp. 60-71.
Ratnayake et al.; "Two New Lactones with Mosquito Larvicidal Activity from Three Hortonia Species"; J. Nat. Prod., 2001, 64, pp. 376-378.
Couladouros, et al; "A General Synthetic Route Towards γ and δ-Lactones. Total Asymmetric Synthesis of (-)-Muricatacin and the Mosquito Oviposition Pheromone (5R,6S)-6-Acetoxy-hexadecanolide"; Tetrahedron Letters 40, 1999, pp. 4861-4862.
Smallegange et al.; "Identification of candidate volatiles that affect the behavioural response of the malaria mosquito Anopheles gambiae sensu stricto to an active kairomone blend: laboratory and semi-field assays"; Physiological Entomology, 2012, 37, pp. 60-71.

CONTROL AND REPELLENCY OF MOSQUITOES

FIELD OF THE INVENTION

This invention relates to compounds used as agents to control and repel mosquitoes.

BACKGROUND TO THE INVENTION

Many mammals, including humans, have suffered the action of mosquitoes. The blood sucking of mosquitoes results in an itching sensation and often a rash. Also, many mosquitoes cause potentially life-threatening illness. *Aedes aegypti* can cause dengue fever and yellow fever, *Anopheles quadrimaculatus* can cause malaria and *Culex quinquefasciatus* can cause West Nile disease. One possible solution to these problems is applying a mosquito repelling agent to the skin as a topical repellent. Applying repellents to fabric, like mosquito netting, is another way of reducing mosquito bites.

DEET®, namely N,N-Diethyl-m-toluamide, is widely used against mosquitoes, but is characterized by an unseemly bad smell, is not particularly long lasting in its effect and it dissolves plastics. Moreover, several safety questions have been raised concerning the use of DEET® and some governments have restricted the amount of the active component that may be employed in formulations. This itself presents a further problem since DEET® is subject to evaporation and it needs to be formulated at higher than effective dosages in order to maintain its effectiveness. Furthermore, many insects and pests have developed resistance to DEET® due to its wide spread usage.

As such, there is a need to provide a mosquito repellent formulation which is non-toxic to the people, plants, and other animals which may be exposed to areas of application. A further need is for a mosquito control formulation that comprises long lasting effects, thereby limiting the need for frequent re-application to treated areas.

Consumer research regarding the key attributes of topically applied insect repellents strongly suggests that consumers prefer products with high efficacy, long-lasting protection, safety in use, and odorless when applied to skin. Leading insect repellent products currently available to consumers claim to meet these requirements but almost always disappoint the user for having unacceptably strong odor on skin.

It must be noted that over the years Researchers have identified ingredients which either matched or exceeded repellency of DEET®, such as for example, U.S. Pat. No. 6,660,288. These were basically fragrance ingredients with added functionality. In the end, these materials failed to become acceptable repellents mainly because of their high cost or intolerably strong odor at levels required to achieve an acceptable level of repellency.

One ingredient among this class of repellents is methyl dihydrojasmonate. It is a well-recognized fragrance ingredient described as having a strong jasmine odor with a citrus freshness. Its popularity as a fragrance ingredient has helped it to become a leading fragrance ingredient representing use volumes in thousands of tons a year. While an elegant fragrance material, its odor intensity represents a problem in using it as a repellent at the required levels of ~15% to match DEET efficacy. It was therefore very surprising to find that propyl dihydrojasmonate, a homolog of methyl dihydrojasmonate, was virtually odorless.

SUMMARY OF THE INVENTION

In accordance with this invention, control and repellency of mosquitoes is obtained by contact of the insects with at least one of the compounds of the structure (I)

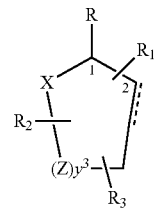

(I)

wherein

R is selected from —OH, =O, —OC(O)R$_4$, —OR$_6$, —(OR$_6$)$_2$, wherein each R$_6$ is independently selected from an alkyl group containing from 1 to 4 carbon atoms and R$_4$ is a branched or straight chain, saturated or unsaturated hydrocarbyl group with zero to two double bonds and from 1 to 15 carbon atoms;

X is O or CH$_2$, with the proviso that when X is O R can only be =O;

each Z is independently selected from (CH) and (CH$_2$);

y is a numeral selected from 1 and 2;

R$_1$ is selected from H or a branched or straight chain, saturated or unsaturated hydrocarbyl group with zero to two double bonds and from 1 to 15 carbon atoms;

R$_2$ is selected from H and a branched or straight chain, saturated or unsaturated hydrocarbyl group with zero to three double bonds and from 1 to 15 carbon atoms;

R$_3$ is selected from H and a branched or straight chain, saturated or unsaturated hydrocarbyl group with zero to three double bonds and from 1 to 15 carbon atoms, —(CH$_2$)$_n$OH, —C(O)OR$_5$, —CH$_2$C(O)OR$_7$, —CH$_2$C(O)R$_8$, —C(O)NR$_9$R$_{10}$, —CH$_2$C(O)NR$_{11}$R$_{12}$ where each of R$_5$, R$_7$, R$_8$, R$_9$, R$_{10}$, R$_{11}$ and R$_{12}$ is independently selected from H and a branched or straight chain, saturated or unsaturated hydrocarbyl group with zero to three double bonds and from 1 to 15 carbon atoms and n is an integer of from 1 to 12;

the bond between the 2 and 3 positions in the ring structure may be a single or a double bond; and wherein the compounds of structure (I) contain from 11 to 20 total carbon atoms in the compounds, with the proviso that when R is =O, X is CH$_2$, Z is CH$_2$, y is 1 R$_2$ is H, and R$_3$ is CH$_2$C(O)OR$_7$ then the total number of carbon atoms in the compounds of structure (I) is from 15 to 20 carbon atoms, and when X is O and R is =O the total number of carbon atoms in the compounds of structure (I) is from 11 to 17 carbon atoms. The invention also includes optical isomers, diastereomers and enantiomers of the named structures. Thus, at all stereocenters where stereochemistry is not explicitly defined, all possible epimers are envisioned. As an aspect of this invention the control of the mosquitoes may be by way of the compounds being toxic to the mosquitoes and larvae thereof.

DETAILED DESCRIPTION OF THE INVENTION

Control and repellency of mosquitoes is obtained by contact of the insects with at least one of the compounds of the structure (I)

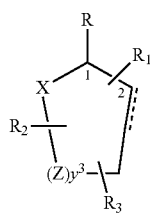

(I)

wherein
R is selected from —OH, ═O, —OC(O)R$_4$, —(OR$_6$)$_2$, wherein each R$_6$ is independently selected from an alkyl group containing from 1 to 4 carbon atoms and R$_4$ is a branched or straight chain, saturated or unsaturated hydrocarbyl group with zero to two double bonds and from 1 to 15 carbon atoms;

X is O or CH$_2$, with the proviso that when X is O R can only be ═O;

each Z is independently selected from (CH) and (CH$_2$);

y is a numeral selected from 1 and 2;

R$_1$ is selected from H or a branched or straight chain, saturated or unsaturated hydrocarbyl group with zero to two double bonds and from 1 to 15 carbon atoms;

R$_2$ is selected from H and a branched or straight chain, saturated or unsaturated hydrocarbyl group with zero to three double bonds and from 1 to 15 carbon atoms;

R$_3$ is selected from H, a branched or straight chain, saturated or unsaturated hydrocarbyl group with zero to three double bonds and from 1 to 15 carbon atoms, —(CH$_2$)$_n$—OH, —C(O)OR$_5$, —CH$_2$C(O)OR$_7$, —CH$_2$C(O)R$_8$, —C(O)NR$_9$R$_{10}$, —CH$_2$C(O)NR$_{11}$R$_{12}$ where each of R$_5$, R$_7$, R$_8$, R$_9$, R$_{10}$, R$_{11}$ and R$_{12}$ is independently selected from H and a branched or straight chain, saturated or unsaturated hydrocarbyl group with zero to three double bonds and from 1 to 15 carbon atoms and n is an integer of from 1 to 12;

the bond between the 2 and 3 positions in the ring structure may be a single or a double bond; and wherein the compounds of structure (I) contain from 11 to 20 total carbon atoms in the compounds, with the proviso that when R is ═O, X is CH$_2$, Z is CH$_2$, y is 1 R$_2$ is H, and R$_3$ is CH$_2$C(O)OR$_7$ then the total number of carbon atoms in the compounds of structure (I) is from 15 to 20 carbon atoms, and when X is O and R is ═O the total number of carbon atoms in the compounds of structure (I) is from 11 to 17 carbon atoms. The invention also includes optical isomers, diastereomers and enantiomers of the named structures. Thus, at all stereocenters where stereochemistry is not explicitly defined, all possible epimers are envisioned. As an aspect of this invention the control of the mosquitoes may be by way of the compounds being toxic to the mosquitoes and larvae thereof.

A preferred group of mosquito control and repellency compounds are those compounds of structure (1) wherein R is ═O or —OH, X is CH$_2$, Z is (CH) or (CH$_2$), y is 1, the bond between positions 2 and 3 is a single bond, R$_1$ is H, R$_2$ is H and R$_3$ is an alkenyl group having at least 11 carbon atoms and 1 or 2 double bonds.

A further preferred group of mosquito control and repellency compounds are those compounds of structure (I) wherein R is ═O or —OH, X is CH$_2$, Z is (CH) or (CH$_2$), y is 1, the bond between positions 2 and 3 is a single bond, R$_1$ is an alkyl group having at least 5 carbon atoms, R$_2$ is H and R$_3$ is —C(O)OR$_5$ and R$_3$ is an alkyl or alkenyl group containing at least 3 carbon atoms.

Another preferred group of mosquito control and repellency compounds are those compounds of structure (I) wherein R is ═O, X is O, Z is CH or CH$_2$, y is 1 or 2, is 1, the bond between positions 2 and 3 is a single bond, R$_1$ is an alkyl group of from 7 to 11 carbon atoms R$_2$ is H and R$_3$ is H or CH$_3$.

An especially preferred group of mosquito control and repellent agents of structure (1) include methyl apritone, propyl dihydrojasmonate, gamma-dodecalactone, gamma methyl dodecalactone, gamma-tridecalactone, gamma methyl tridecalactone, gamma-tetradecalactone, 3-methyl-5-butyl-2-cyclohexenone and 3-methyl-5-heptyl-2-cyclohexenone.

Representative examples of compounds of structure (I) include, but are not limited to,

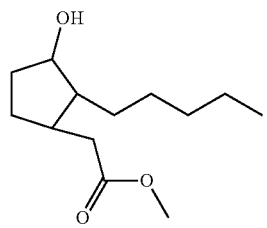

methyl 2-(3-hydroxy-2-pentylcyclopentyl)acetate
Chemical Formula: C$_{13}$H$_{24}$O$_3$
Molecular Weight: 228.33
Methyl Dihydro Jasmolate

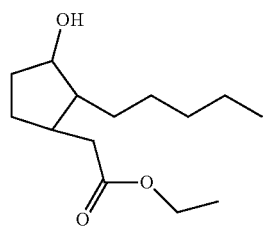

ethyl 2-(3-hydroxy-2-pentylcyclopentyl)acetate
Chemical Formula: C$_{14}$H$_{26}$O$_3$
Molecular Weight: 242.35
Ethyl Dihydro Jasmolate

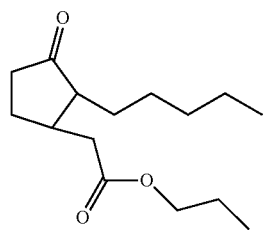

propyl 2-(3-oxo-2-pentylcyclopentyl)acetate
Chemical Formula: C$_{15}$H$_{26}$O$_3$
Molecular Weight: 254.37
Propyl Dihydro Jasmonate -continued

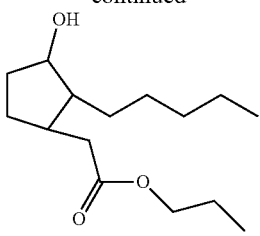

propyl 2-(3-hydroxy-2-pentylcyclopentyl)acetate
Chemical Formula: $C_{15}H_{28}O_3$
Molecular Weight: 256.38
Propyl Dihydro Jasmolate

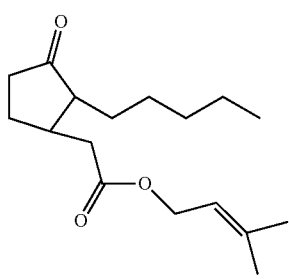

3-methylbut-2-enyl 2-(3-oxo-2-pentylcyclopentyl)acetate
Chemical Formula: $C_{17}H_{28}O_3$
Molecular Weight: 280.40
Prenyl Dihydro Jasmonate

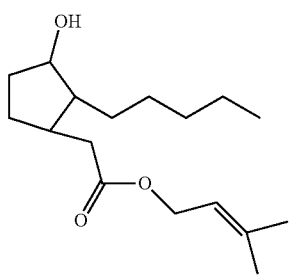

3-methylbut-2-enyl 2-(3-hydroxy-2-pentylcyclopentyl)acetate
Chemical Formula: $C_{17}H_{30}O_3$
Molecular Weight: 282.42
Prenyl Dihydro Jasmolate

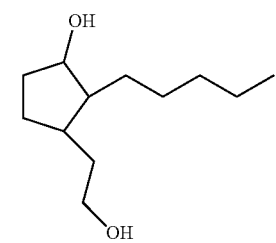

3-(2-hydroxyethyl)-2-pentylcyclopentanol
Chemical Formula: $C_{12}H_{24}O_2$
Molecular Weight: 200.32
MethylDihydroJasmodiol -continued

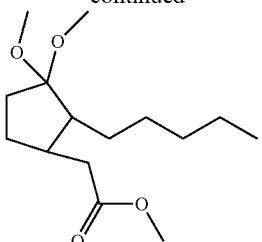

methyl 2-(3,3-dimethoxy-2-pentylcyclopentyl)acetate
Chemical Formula: $C_{15}H_{28}O_4$
Molecular Weight: 272.38
Methyl Dihydro Jasmonate Dimethyl Ketal

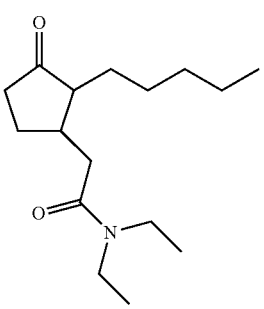

N,N-diethyl-2-(3-oxo-2-pentylcyclopentyl)acetamide
Chemical Formula: $C_{16}H_{29}NO_2$
Molecular Weight: 267.41
MDJ Amide

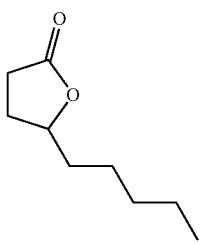

gamma Nonalactone
Chemical Formula: $C_9H_{16}O_2$
Molecular Weight: 156.22

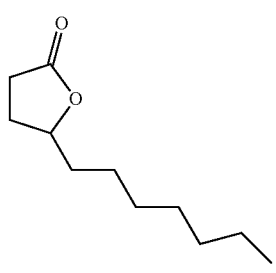

gamma Undecalactone
Chemical Formula: $C_{11}H_{20}O_2$
Molecular Weight: 184.28

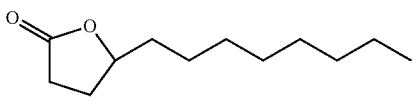

5-octyldihydrofuran-2(3H)-one
Chemical Formula: $C_{12}H_{22}O_2$
Molecular Weight: 198.30
gamma-dodecalactone

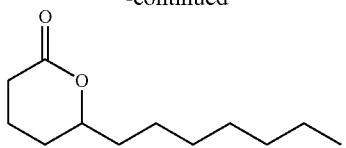

2H-Pyran-2-one, 6-heptyltetrahydro-
Chemical Formula: $C_{12}H_{22}O_2$
Molecular Weight: 198.31
Delta Dodecalactone

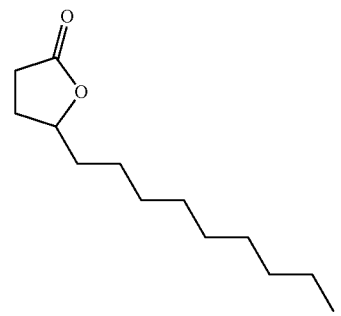

5-nonyldihydrofuran-2(3H)-one
Chemical Formula: $C_{13}H_{24}O_2$
Molecular Weight: 212.33
Gamma-Tridecalactone

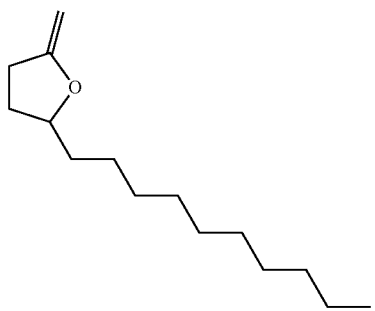

5-decyldihydrofuran-2(3H)-one
Chemical Formula: $C_{14}H_{26}O_2$
Molecular Weight: 226.36
Gamma-Tetradecalactone

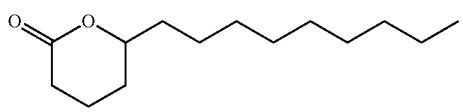

6-nonyltetrahydro-2H-pyran-2-one
Chemical Formula: $C_{14}H_{26}O_2$
Molecular Weight: 226.36
Delta-Tetradecalactone

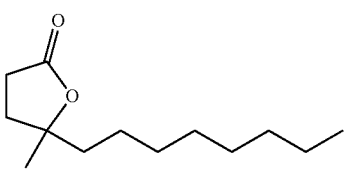

Gamma Methyl Dodecalactone
2(3H)-Furanone, 5-octyldihydro-5-methyl-

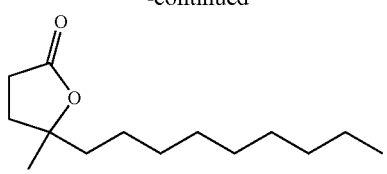

gamma Methyl Tridecalactone
5-methyl-5-nonyldihydrofuran-2(3H)-one
4-methyl-4-nonyl gamma butyrolactone
C14 lactone

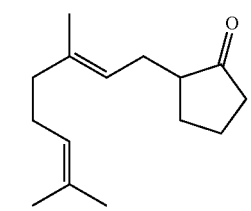

(E)-2-(3,7-dimethylocta-2,6-dienyl)cyclopentanone
Chemical Formula: $C_{15}H_{24}O$
Molecular Weight: 220.35
Apritone

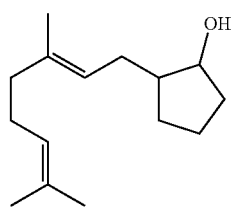

(E)-2-(3,7-dimethylocta-2,6-dienyl)cyclopentanol
Chemical Formula: $C_{15}H_{26}O$
Molecular Weight: 222.37
Apritol

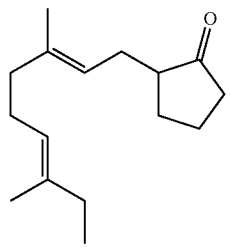

2-((2E,6E)-3,7-dimethylnona-2,6-dienyl)cyclopentanone
Chemical Formula: $C_{16}H_{26}O$
Molecular Weight: 234.38
Methyl Apritone

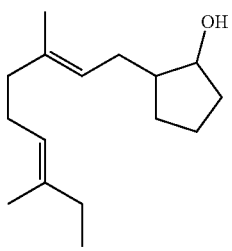

2-((2E,6E)-3,7-dimethylnona-2,6-dienyl)cyclopentanol
Chemical Formula: $C_{16}H_{28}O$
Molecular Weight: 236.39
Methyl Apritol -continued

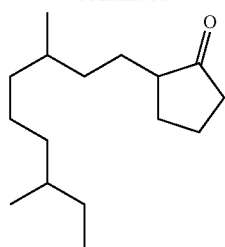

2-(3,7-dimethylnonyl)cyclopentanone
Chemical Formula: $C_{16}H_{30}O$
Molecular Weight: 238.41
Tetrahydromethyl Apritone

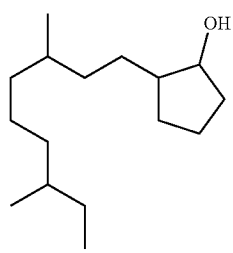

2-(3,7-dimethylnonyl)cyclopentanol
Chemical Formula: $C_{16}H_{32}O$
Molecular Weight: 240.42
Tetrahydromethyl Apritol

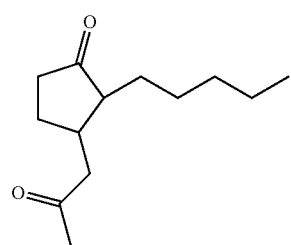

3-(2-oxopropyl)-2-pentylcyclopentanone
Chemical Formula: $C_{13}H_{22}O_2$
Molecular Weight: 210.31
Amyl Cyclopentanone Propanone

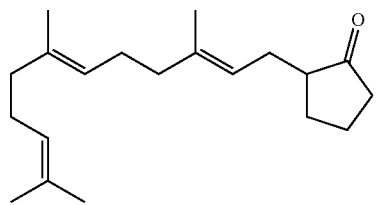

2-((2E,6E)-3,7,11-trimethyldodeca-2,6,10-trienyl)cyclopentanone
Chemical Formula: $C_{20}H_{32}O$
Molecular Weight: 288.47
Farnesylcyclopentanone

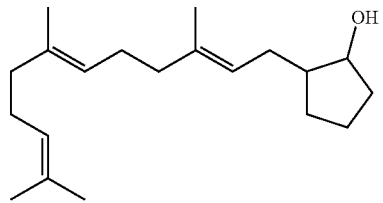

2-((2E,6E)-3,7,11-trimethyldodeca-2,6,10-trienyl)cyclopentanol
Chemical Formula: $C_{20}H_{34}O$
Molecular Weight: 290.48
Farnesylcyclopentanol -continued

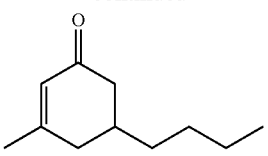

Chemical Formula: $C_{11}H_{18}O$
Molecular Weight: 166.26
3-methyl-5-butyl-2-cyclohexenone

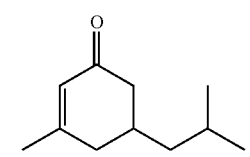

Chemical Formula: $C_{11}H_{18}O$
Molecular Weight: 166.26
3-methyl-5-isobutyl-2-cyclohexenone

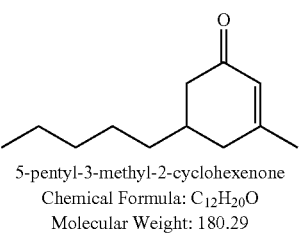

5-pentyl-3-methyl-2-cyclohexenone
Chemical Formula: $C_{12}H_{20}O$
Molecular Weight: 180.29

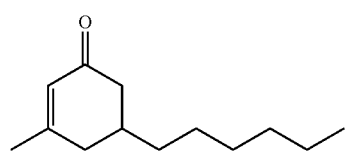

Chemical Formula: $C_{13}H_{22}O$
Molecular Weight: 194.31
3-methyl-5-hexyl-2-cyclohexenone

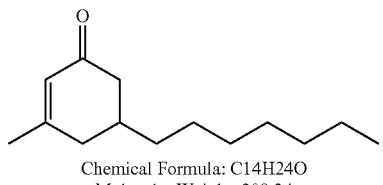

Chemical Formula: $C_{14}H_{24}O$
Molecular Weight: 208.34
3-methyl-5-heptyl-2-cyclohexenone

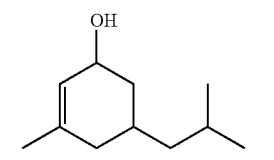

Chemical Formula: $C_{11}H_{20}O$
Molecular Weight: 168.28
3-methyl-5-isobutyl-2-cyclohexen-1-ol

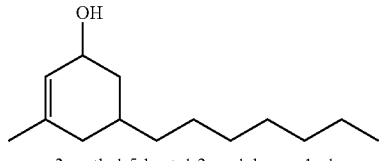

3-methyl-5-heptyl-2-cyclohexen-1-ol
Chemical Formula: $C_{14}H_{26}O$
Molecular Weight: 210.36

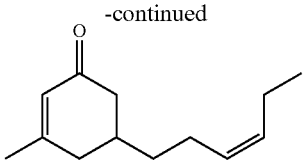

Chemical Formula: C13H20O
Molecular Weight: 192.30
3-methyl-5-(z-3-hexenyl)-2-cyclohexenone

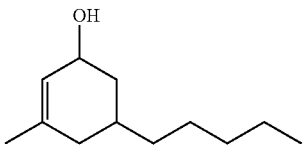

3-methyl-5-pentyl-2-cyclohexen-1-ol
Chemical Formula: C12H22O
Molecular Weight: 182.30

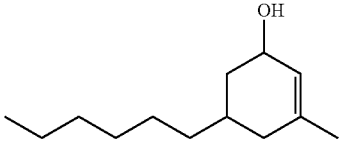

3-methyl-5-hexyl-2-cyclohexenol
Chemical Formula: $C_{13}H_{24}O$
Molecular Weight: 196.18

The active compounds of structure (I) may be formulated into any suitable formulations such as for example, including but not limited to, solutions, oils, creams, lotions, shampoos, aerosols or the like. Traditional inert carriers such as, including but not limited to, alcohols, esters and petroleum distillates, could be used to produce formulations of the active compounds to be used as repellent formulations. Another series of carriers are the biodegradable oils, including but not limited to, the Olestra® family of oils, isopropyl myristate and squalane.

When the formulation will be used as an aerosol, it is preferable to add a propellant. Suitable propellants include propane, butane, isobutane, dimethyl ether, carbon dioxide, nitrous oxide, nitrogen, and combinations thereof.

The amount of active compound of structure (I) utilized in any control or repellent formulation will depend upon the type of formulation used and the particular mosquito against which the formulation is employed but will generally range from about 1% to about 30% by weight in a carrier.

The active control compounds of structure (I) may be applied to surfaces of or impregnated in clothing or fabric. The active ingredients may be applied to fabrics such as, but not limited to mosquito nets. The amount of active material can be about 0.025 g/ft$^2$ to about 3.6 g/ft$^2$.

The active ingredients may also be applied to outdoor materials such as, but not limited to, lawns, trees, shrubbery, or flooring to prevent the mosquitoes from resting there.

The formulations described above can be prepared by any convenient means, e.g., by mixing the active compound or active compounds with one or more other carriers or vehicles such as, including but not limited to, those described herein before. In addition, active components of structure (I) may be blended with existing active repellents or toxicants including, but not limited to, DEET® and p-Menthane-3,8-diol (PMD).

As will be shown in the tables below, there is a synergistic effect with combinations of compounds.

In each application, it can be noted that the epi isomer of propyl dihydrojasmonate is preferential in terms of repellency.

The invention is illustrated by, but not limited to, the following examples.

Five replicates of 250 adult female mosquitoes each were placed in clear plastic cages with access to five warmed, blood-filled, membrane-covered wells. The mosquitoes were Aedes aegypti unless otherwise noted. Membranes were treated with repellent. Five replicates were tested. Each replicate used a fresh batch of mosquitoes, blood and treated membranes. The number of mosquitoes probing each well was recorded at two minute intervals for 20 minutes. The total numbers of probes on each well were tallied at the end of the observation period and the average percentage repellency relative to the control was calculated for each formulation.

The results are given below in Table 1.

TABLE 1

| Samples diluted in isopropanol unless otherwise noted. | Avg % Repellency | Avg # Probes |
|---|---|---|
| 4% DEET ® | 90.8 | 8.4 |
| 10% DEET ® | 98 | 0.8 |
| 7% para-menthane-3,8-diol (PMD) | 79.2 | 9 |
| 7% methyl apritol | 91.9 | 6.6 |
| 10% methyl apritol | 89.2 | 6.8 |
| 7% methyl apritone | 90.4 | 7.6 |
| 10% methyl apritone | 93.9 | 3.6 |
| 7% tetrahydroapritone | 93.7 | 3.8 |
| 7% tetrahydromethyl apritone | 74.9 | 11 |
| 4% Methyl Dihydrojasmolate | 98.8 | 0.6 |
| 7% Methyl Dihydrojasmolate | 100 | 0 |
| 7% Ethyl Dihydrojasmolate | 100 | 0 |
| 7% Prenyl Dihydrojasmolate | 92.2 | 3.2 |
| 5% Propyl Dihydrojasmonate (PDJ) | 97 | 4 |
| 7% Propyl Dihydrojasmonate (PDJ) | 95.6 | 2.6 |
| 2.5% Propyl Dihydrojasmonate - high epi | 95 | 2 |
| 2.5% Propyl Dihydrojasmonate - low epi | 85 | 6 |
| 5% PDJ in squalane | 99 | 0 |
| 7% Prenyl Dihydrojasmonate | 92.6 | 2.8 |
| 7% Hexyl Dihydrojamonate | 66.1 | 30.4 |
| 2.5% methyl dihydrojasmonate amide | 55 | 18.6 |
| 5% methyl dihydrojasmonate amide | 90.1 | 6.8 |
| 7% dihydrojasmindiol | 84.3 | 7.2 |
| 7% dihydrojasmolactone | 100 | 0 |
| 7% gamma-nonalactone | 77.1 | 20.4 |
| 7% gamma-undecalactone | 100 | 0 |
| 7% delta-dodecalactone | 100 | 0 |
| 7% gamma-dodecalactone | 100 | 0 |
| 5% gamma Methyl Dodecalactone | 98 | 1 |
| 5% gamma-tridecalactone | 94.4 | 3.1 |
| 7% gamma-tridecalactone | 97.5 | 1.8 |
| 5% gamma Methyl Tridecalactone | 96 | 4 |
| 7% delta-tetradecalactone | 97.3 | 1.6 |
| 7% gamma-tetradecalactone | 98.9 | 0.8 |
| 7% amyl cyclopentanone propanone | 100 | 0 |
| 7% farnesyl cyclopentanol | 67.8 | 16.2 |
| 5% 3-methyl-5-butyl-2-cyclohexenone | 97 | 1 |
| 5% 3-methyl-5-hexyl-2-cyclohexenone | 100 | 0 |
| 5% 3-methyl-5-hexyl-2-cyclohexenol | 91 | 1 |
| 5% 3-methyl-5-heptyl-2-cyclohexenone | 99 | 0 |
| 5% of 50:50 mix of PMD and Methyl Apritone | 96 | 3 |
| 5% of 50:50 mix of PMD:PDJ | 98 | 1 |
| 5% of 50:50 mix of DEET:PDJ | 99 | 1 |
| 5% of 50:50 mix of PDJ:gamma Methyl Tridecalactone | 93 | 3 |
| 5% of 50:50 mix of PMD:gamma Methyl Tridecalactone | 100 | 0 |
| 5% of 50:50 mix of PMD:gamma Tridecalactone | 99 | 0 |
| Culex quinquefasciatus | | |
| 7% gamma-dodecalactone | 100 | 0 |
| 7% methyl apritone | 100 | 0 |

In addition, human testing was performed to determine the efficacy of compounds from structure (I). Mosquito species used are described in the tables below.

Each test subject was exposed to 2 products each test day. The application rate was between 0.65 ml and 1 ml/250 cm$^2$ for all repellents. The actual amount of repellent used was based upon the amount that provides thorough coverage of the 250 cm$^2$ treatment area. A repellent was applied using either a micropipette or a syringe minus the needle. The repellents were then evenly spread on the treatment area with a gloved finger.

Each test subject's forearms were allowed to air dry for approximately 30 minutes prior to the first exposure. The study coordinator or technician assisted the test subjects in inserting their arms into the test cages containing 200 mosquitoes, taking care not to rub them on the cloth sleeve, to confirm that the insects were biting. If fewer than 10 mosquitoes land on the untreated arm in 60 seconds (all would normally bite), fresh mosquitoes will be added. Typically, the ten (10) landings took place within 10-30 seconds. Both treated arms were inserted into a cage; there were two subjects (4 arms) per cage. The test subjects exposed their treated forearms to the mosquitoes in the test cages for 5 minutes. The subjects then remove their arms from the cages with assistance from the study coordinator or a technician. Exposures of each arm were repeated every 30 minutes until the repellent on that arm was determined to be no longer effective ('breakdown') or until 8 hours have elapsed, whichever occurred first.

Breakdown occurs when the first confirmed bite is noted. A confirmed bite occurs when a bite is followed by a second bite in the same exposure period or in the next succeeding exposure period. The second bite becomes the confirming bite and the breakdown time is taken as the time of the first bite. The average of two repetitions is given. Results are reported in Table 2.

TABLE 2

| Aedes aegypti | |
|---|---|
| Compound, diluted in isopropanol unless otherwise noted | 100% bite protection time |
| 5% p-menthane-3,8-diol(PMD) | 2.75 hr |
| 10% p-menthane-3,8-diol | 6.25 hr |
| 10% methyl apritone | <0.5 hr |
| 10% gamma-dodecalactone | 1.25 hr |
| 30% gamma-tridecalactone | 1 hr |
| 15% gamma-tetradecalactone | 0.5 hr |
| 15% propyl dihydrojasmonate | <0.5 hr |
| 30% propyl dihydrojasmonate | 1 hr |
| 7% pmd and 23% propyl dihydrojasmonate | 6.5 hr |
| 7% pmd and 15% gamma-tridecalactone | 6 hr |
| 10% pmd and 15% propyl dihydrojasmonate | >8 hr |
| 30% propyl dihydrojasmonate in squalane | 2.75 hr |
| 10% pmd and 15% gamma-tridecalactone | 7 hr |
| 10% pmd and 15% gamma methyl tridecalactone | 2 hr |
| Compound | 100% bite protection time |
| Culex quinquefasciatus | |
| 10% PMD | 4.25 hr |
| 10% PMD and 15% propyl dihydrojasmonate | >8 hr |
| 10% PMD and 15% gamma-tridecalactone | >8 hr |
| Anopheles quadrimaculatus | |
| 10% PMD | 6.75 hr |
| 10% PMD AND 15% propyl dihydrojasmonate | >8 hr |
| 10% PMD AND 15% gamma-tridecalactone | >8 hr |

A test was designed to determine if two test samples at 2 concentrations applied to a surface are toxic to mosquitoes. Aluminum foil squares, 5'×5' were treated with one of the test samples and after drying were placed on top of large Petri dishes, 6" in diameter. Inverted polystyrene cups, 3.5" in diameter and 3" high, each with a circular hole drilled through the bottom, and the sides and top painted with Fluon, were used as the treatment containers. They were placed on top of the Petri dishes and secured with rubber bands. Mosquitoes were aspirated and gently blown through the drilled hole into the arena. A plastic disc was then placed over the hole. Five replicates of ten female Aedes aegypti were used for the test sample treatment and an additional 5 replicates of 10 mosquitoes were used for solvent control. Mosquitoes were constantly exposed to the dried test material for 5 minutes, after which time they were transferred into clean containers, where they were provided a sucrose solution for nourishment. The formal observations for knockdown were made at 1 and 4 hours. At 24 hours the numbers of live, moribund and dead mosquitoes were counted.

TABLE 3

| Compound, diluted in ethanol | 1 hr knock-down | 4 hr knock-down | 24 hr mortality |
|---|---|---|---|
| Ethanol control | 2% | 4% | 4% |
| 2.5% 3-methyl-5-butyl-2-cyclohexenone | 100% | 100% | 88% |
| 2.5% 3-methyl-5-heptyl-2-cyclohexenone | 100% | 100% | 98% |

Odor intensity measurement results reported here establish that propyl dihydrojasmonate meets the "odor free" topical repellent requirements far better than methyl dihydrojasmonate and other leading actives currently in use to formulate topical insect repellents.

Humans perceive odor in terms of intensity and hedonics (character). Odor intensity is the measure of the perceived strength of an odor above its threshold. Odor intensity is an objective property and can be measured reliably and reproducibly by a panel using well accepted scientific psychophysical methodologies. Results from these measurements are described in categories which progress from "no odor", then "very weak", through to "very strong". On the other hand, odor hedonics or character is the degree to which an odor is perceived as "pleasant or unpleasant" or "liked or disliked". Therefore, hedonics represent a subjective quality of odor and considerable variations are experienced in its measurement, primarily influenced by individual preferences and past life experiences of the panel members.

Regulatory bodies world over have established robust test methodologies for the assessment of odor intensity in work and public places. These methodologies apply psychophysical principles to measuring and have set up rigorous limits to the permissible levels of odor intensity in the environment. Using a similar approach, designed after the ASTM standard E544-10, we have compared the relative odor intensities of methyl dihydrojasmonate and propyl dihydrojasmonate. Surprisingly, we found that propyl dihydrojasmonate is very different in having almost no odor in comparison. Results from this test are presented in table 1 below.

ASTM standard E544-10 outlines a preferred test methodology for referencing and measuring the odor intensity of a material in the suprathreshold region. The tests reported here use a slightly modified static-scale ASTM method in which reference odorant is 1-butanol. The scale has a forced choice of six intensity levels and the unknown sample is matched to the static scale by a trained professional perfumer. Results are reported in Table 4.

TABLE 4

| Compound at 15% | Test material Intensity score |
|---|---|
| Methyl Dihydrojasmonate | 5 |
| DEET ® | 1.5 |
| Propyl Dihydrojasmonate | 1 |
| Odor Strength Level | |
| Extremely strong | 6 |
| Very strong | 5 |
| Strong | 4 |
| Moderate | 3 |
| Weak | 2 |
| Very weak | 1 |
| No odor | 0 |

These results are surprising since prior literature suggests that a certain volatility of compounds is necessary for repellency. However, the above results and the data of this invention unexpectedly demonstrate that higher molecular weight compounds of lesser volatility, often well below the generally accepted lower limit of volatility, are equal to or better repellents that compounds of higher volatility.

It was therefore surprising to find that propyl dihydrojasmonate with a boiling point of 356 C was uniquely appropriate to provide the desired vapor concentration over the skin needed for a prolonged repellency of 8 hours or more without the use of polymers or other inert ingredients. This unexpected balance between high repellency and required longevity makes propyl dihydrojasmonate an active of choice in formulating a cost effective odorless or low odor repellent capable of delivering long lasting protection to the consumer.

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

I claim:

1. A method for the control or repellency of mosquitoes, the method comprising bringing mosquitoes into contact with at least one of the compounds of the structure (I)

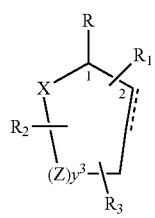

(I)

wherein

R is =O or —OH, X is $CH_2$, Z is (CH) or ($CH_2$), y is 1, the bond between positions 2 and 3 is a single bond, $R_1$ is H, $R_2$ is H, and $R_3$ is an alkyl group having at least 11 carbon atoms or an alkenyl group having at least 10 carbon atoms and 1 or 2 double bonds; or R is =O or —OH, X is $CH_2$, Z is (CH) or ($CH_2$), y is 1, the bond between positions 2 and 3 is a single bond, $R_1$ is an alkyl group having at least 5 carbon atoms, $R_2$ is H, and $R_3$ is —C(O)O$R_5$, and $R_5$ is an alkyl or alkenyl group containing at least 3 carbon atoms;or R is =O, X is O, Z is CH or $CH_2$, y is 1 or 2, the bond between positions 2 and 3 is a single bond, $R_1$ is an alkyl group of from 5 to 11 carbon atoms, $R_2$ is H, and $R_3$ is H or $CH_3$.

2. A method for the control or repellency of mosquitoes, the method comprising bringing mosquitoes into contact with at least one of the compounds of the structure

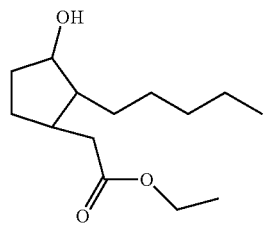

ethyl 2-(3-hydroxy-2-pentylcyclopentyl)acetate
Chemical Formula: $C_{14}H_{26}O_3$
Molecular Weight: 242.35
Ethyl Dihydro Jasmolate

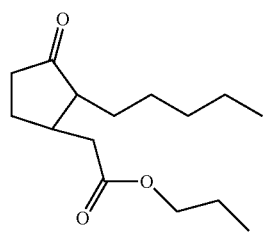

propyl 2-(3-oxo-2-pentylcyclopentyl)acetate
Chemical Formula: $C_{15}H_{26}O_3$
Molecular Weight: 254.37
Propyl Dihydro Jasmonate

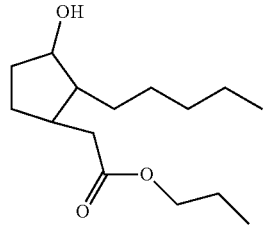

propyl 2-(3-hydroxy-2-pentylcyclopentyl)acetate
Chemical Formula: $C_{15}H_{28}O_3$
Molecular Weight: 256.38
Propyl Dihydro Jasmolate

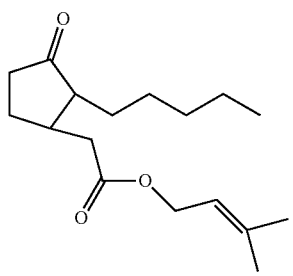

3-methylbut-2-enyl 2-(3-oxo-2-pentylcyclopentyl)acetate
Chemical Formula: $C_{17}H_{28}O_3$
Molecular Weight: 280.40
Prenyl Dihydro Jasmonate

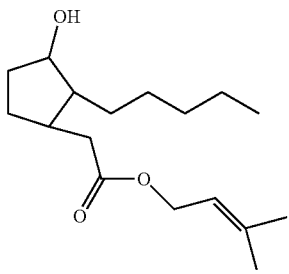

3-methylbut-2-enyl 2-(3-hydroxy-2-pentylcyclopentyl)acetate
Chemical Formula: $C_{17}H_{30}O_3$
Molecular Weight: 282.42
Prenyl Dihydro Jasmolate

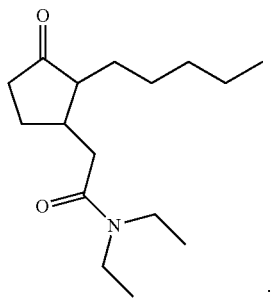

N,N-diethyl-2-(3-oxo-2-pentylcyclopentyl)acetamide
Chemical Formula: $C_{16}H_{29}NO_2$
Molecular Weight: 267.41
MDJ Amide 3. The method according to claim 1 wherein the at least one compound of structure (I) is selected from the group consisting of:

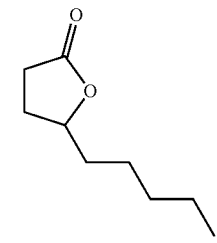

gamma Nonalactone
Chemical Formula: $C_9H_{16}O_2$
Molecular Weight: 156.22

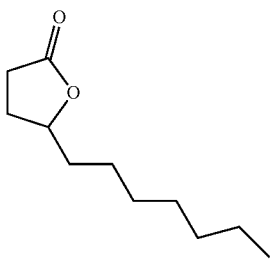

gamma Undecalactone
Chemical Formula: $C_{11}H_{20}O_2$
Molecular Weight: 184.28

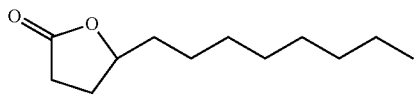

5-octyldihydrofuran-2(3H)-one
Chemical Formula: $C_{12}H_{22}O_2$
Molecular Weight: 198.30
gamma-dodecalactone

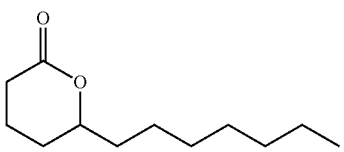

2H-Pyran-2-one, 6-heptyltetrahydro-
Chemical Formula: $C_{12}H_{22}O_2$
Molecular Weight: 198.31
Delta Dodecalactone

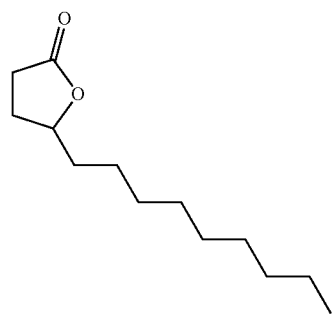

5-nonyldihydrofuran-2(3H)-one
Chemical Formula: $C_{13}H_{24}O_2$
Molecular Weight: 212.33
Gamma-Tridecalactone

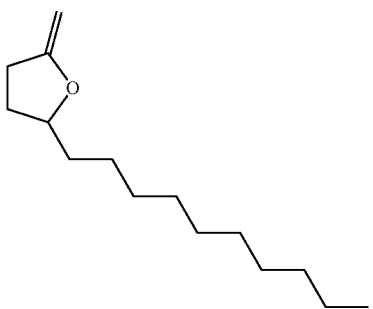

5-decyldihydrofuran-2(3H)-one
Chemical Formula: $C_{14}H_{26}O_2$
Molecular Weight: 226.36
Gamma-Tetradecalactone

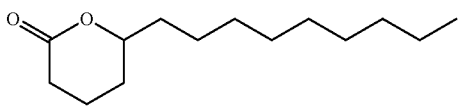

6-nonyltetrahydro-2H-pyran-2-one
Chemical Formula: $C_{14}H_{26}O_2$
Molecular Weight: 226.36
Delta-Tetradecalactone -continued

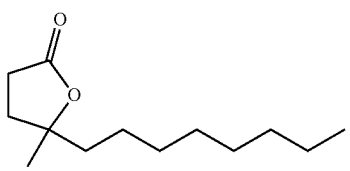

Gamma Methyl Dodecalactone
2(3H)-Furanone, 5-octyldihydro-5-methyl-

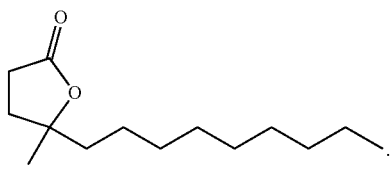

gamma Methyl Tridecalactone
5-methyl-5-nonyldihydrofuran-2(3H)-one
4-methyl-4-nonyl gamma butyrolactone
C14 lactone

4. The method according to claim 1 wherein the at least one compound of structure (I) is selected from the group consisting of

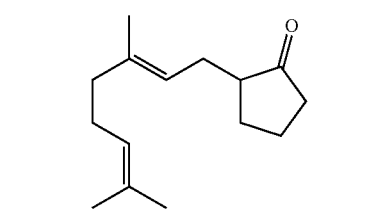

(E)-2-(3,7-dimethylocta-2,6-dienyl)cyclopentanone
Chemical Formula: $C_{15}H_{24}O$
Molecular Weight: 220.35
Apritone

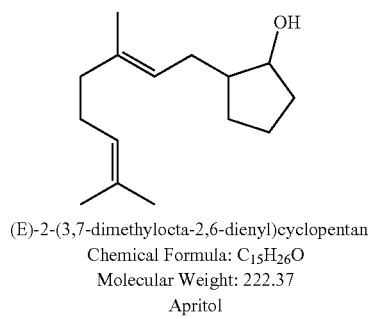

(E)-2-(3,7-dimethylocta-2,6-dienyl)cyclopentanol
Chemical Formula: $C_{15}H_{26}O$
Molecular Weight: 222.37
Apritol

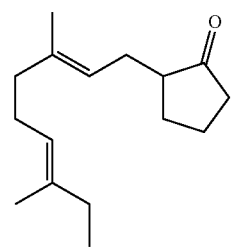

2-((2E,6E)-3,7-dimethylnona-2,6-dienyl)cyclopentanone
Chemical Formula: $C_{16}H_{26}O$
Molecular Weight: 234.38
Methyl Apritone -continued

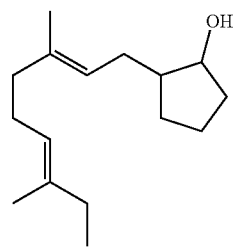

2-((2E,6E)-3,7-dimethylnona-2,6-dienyl)cyclopentanol
Chemical Formula: $C_{16}H_{28}O$
Molecular Weight: 236.39
Methyl Apritol

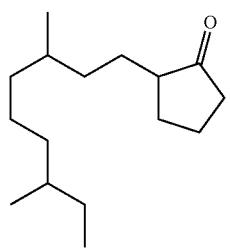

2-(3,7-dimethylnonyl)cyclopentanone
Chemical Formula: $C_{16}H_{30}O$
Molecular Weight: 238.41
Tetrahydromethyl Apritone

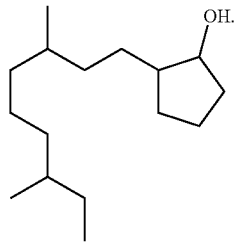

2-(3,7-dimethylnonyl)
cyclopentanol
Chemical Formula: $C_{16}H_{32}O$
Molecular Weight: 240.42
Tetrahydromethyl Apritol

5. A method for the control or repellency of mosquitoes, the method comprising bringing mosquitoes into contact with at least one of the compounds of the structure

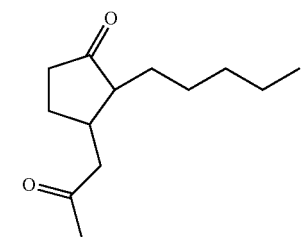

3-(2-oxopropyl)-2-pentylcyclopentanone
Chemical Formula: $C_{13}H_{22}O_2$
Molecular Weight: 210.31
Amyl Cyclopentanone Propanone

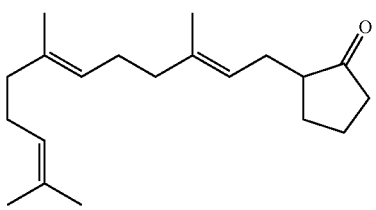

2-((2E,6E)-3,7,11-trimethyldodeca-2,6,10-trienyl)cyclopentanone
Chemical Formula: C$_{20}$H$_{32}$O
Molecular Weight: 288.47
Farnesylcyclopentanone.

6. A method for the control or repellency of mosquitoes, the method comprising bringing mosquitoes into contact with at least one of the compounds of the structure

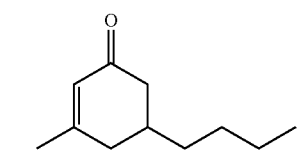

Chemical Formula: C11H18O
Molecular Weight: 166.26
3-methyl-5-butyl-2-cyclohexenone

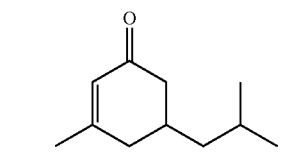

Chemical Formula: C11H18O
Molecular Weight: 166.26
3-methyl-5-isobutyl-2-cyclohexenone

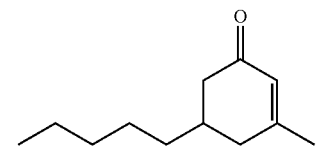

5-pentyl-3-methyl-2-cyclohexenone
Chemical Formula: C$_{12}$H$_{20}$O
Molecular Weight: 180.29

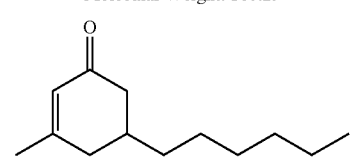

Chemical Formula: C13H22O
Molecular Weight: 194.31
3-methyl-5-hexyl-2-cyclohexenone

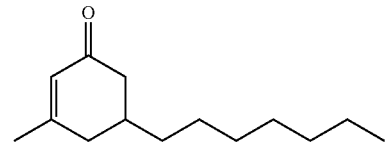

Chemical Formula: C14H24O
Molecular Weight: 208.34
3-methyl-5-heptyl-2-cyclohexenone

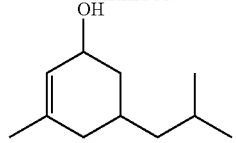

Chemical Formula: C11H20O
Molecular Weight: 168.28
3-methyl-5-isobutyl-2-cyclohexen-1-ol

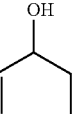

3-methyl-5-heptyl-2-cyclohexen-1-ol
Chemical Formula: C14H26O
Molecular Weight: 210.36

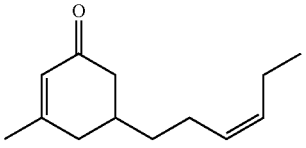

Chemical Formula: C13H20O
Molecular Weight: 192.30
3-methyl-5-(z-3-hexenyl)-2-cyclohexenone

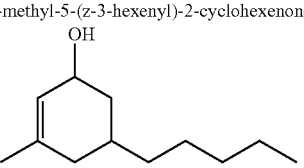

3-methyl-5-pentyl-2-cyclohexen-1-ol
Chemical Formula: C12H22O
Molecular Weight: 182.30

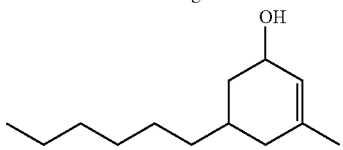

3-methyl-5-hexyl-2-cyclohexenol
Chemical Formula: C$_{13}$H$_{24}$O
Molecular Weight: 196.18

7. The method according to claim 1 wherein the at least one compound of structure (I) is applied to surface of or impregnated into clothing of fabric.

8. The method according to claim 1 wherein the compound of structure (I) is applied topically in the form of lotion, wipes, or sprays.

9. The method according to claim 1 wherein the mosquito is brought into contact with at least one of the compounds of structure (I) in combination with a compound selected from N,N-diethyl-m-toluamide and para-menthane-3,8-diol.

10. The method according to claim 1 wherein the at least one compound of structure (I) is selected for methyl apritone, propyl dihydrojasmonate, gamma-dodecalactone, gamma methyl dodecalactone, gamma-tridecalactone, gamma methyl tridecalactone, gamma-tetradecalactone, 3-methyl-5-butyl-2-cyclohexenone and 3-methyl-5-heptyl-2-cyclohexenone.

11. The method according to claim 1 wherein the at least one compound of structure (I) is
is toxic to mosquitoes or larvae thereof.

12. A method for the control or repellency of mosquitoes, the method comprising bringing mosquitoes into contact with at least one of the compounds of the structure (I)

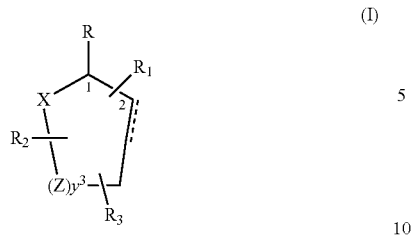
wherein
R is =O or —OH, X is $CH_2$, Z is (CH) or ($CH_2$), y is 1, the bond between positions 2 and 3 is a single bond, $R_1$ is an alkyl group having at least 5 carbon atoms, $R_2$ is H, and $R_3$ is —$CH_2C(O)OR_7$ or an amide group, and $R_7$ is an alkyl or alkenyl group containing at least 2 carbon atoms.
* * * * *